(12) United States Patent
Van Gool et al.

(10) Patent No.: US 12,285,209 B2
(45) Date of Patent: Apr. 29, 2025

(54) PERSONAL CARE DEVICE CONFIGURED TO PERFORM A LIGHT-BASED HAIR REMOVAL

(71) Applicant: KONINKLIJKE PHILIPS N.V., Eindhoven (NL)

(72) Inventors: Edgar Van Gool, Noord-Brabant (NL); Felix Godfried Peter Peeters, Heide (NL); Marjolein Yvonne Jansen, Eindhoven (NL); Eyob Atanfu Amra, Noord Barabant (NL); Eric Gerard Marie Van Kempen, Eindhoven (NL); Lars Christian Casper, Den Bosch (NL); Wilbert Bernard Roger Pennings, Best (NL); Tim Tielemans, Heeze (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 303 days.

(21) Appl. No.: 17/919,392

(22) PCT Filed: Apr. 14, 2021

(86) PCT No.: PCT/EP2021/059613
§ 371 (c)(1),
(2) Date: Oct. 17, 2022

(87) PCT Pub. No.: WO2021/213852
PCT Pub. Date: Oct. 28, 2021

(65) Prior Publication Data
US 2023/0149077 A1    May 18, 2023

(30) Foreign Application Priority Data
Apr. 21, 2020 (EP) .................................. 20170690

(51) Int. Cl.
*A61B 18/18* (2006.01)
*A61B 18/00* (2006.01)

(52) U.S. Cl.
CPC .... *A61B 18/18* (2013.01); *A61B 2018/00476* (2013.01)

(58) Field of Classification Search
None
See application file for complete search history.

(56) References Cited

U.S. PATENT DOCUMENTS 7,220,254 B2 * 5/2007 Altshuler ............... A61B 90/30
606/9
7,309,335 B2 * 12/2007 Altshuler ............. A61N 5/0616
606/9
(Continued)

FOREIGN PATENT DOCUMENTS

EP    2499985 A1    9/2012
EP    3228210 A1    10/2017
(Continued)

OTHER PUBLICATIONS

International Search Report and Written Opinion of PCT/EP2021/059613, dated May 10, 2021.

*Primary Examiner* — Shirley X Jian

(57) ABSTRACT

According to an aspect, there is provided a personal care device (52) for performing a light-based hair removal or photo-epilation operation on a body of a subject. The personal care device (52) comprises a housing (54) that includes a first window or opening (68), a light source configured to generate light to perform the light-based hair removal or photo-epilation operation, wherein the light source is arranged in the housing such that light emitted by the light source illuminates a part of the body, a receiving member in or on the housing (54) for receiving and retaining a consumer electronic device (62) in or on the personal care (Continued)

device (52), and an optical system (80) in the housing (54) for enabling an imaging unit (78) of a consumer electronic device (62) retained in the recess (60) to obtain images of a part of the body via the first window or opening (68).

14 Claims, 5 Drawing Sheets

(56) References Cited

U.S. PATENT DOCUMENTS

| | | | |
|---|---|---|---|
| 8,672,926 B2 | 3/2014 | Van Hal | |
| 10,404,890 B2 | 9/2019 | Cao | |
| 11,676,276 B2* | 6/2023 | Dacosta | A61B 5/445 |
| | | | 382/128 |
| 11,954,861 B2* | 4/2024 | DaCosta | A61B 5/0077 |
| 11,961,236 B2* | 4/2024 | Dacosta | A61B 5/0071 |
| 2005/0154381 A1* | 7/2005 | Altshuler | A61B 90/30 |
| | | | 606/9 |
| 2005/0154382 A1* | 7/2005 | Altshuler | A61B 18/203 |
| | | | 606/9 |
| 2006/0253176 A1* | 11/2006 | Caruso | A61B 18/203 |
| | | | 607/88 |
| 2008/0147054 A1* | 6/2008 | Altshuler | A61B 90/37 |
| | | | 606/9 |
| 2017/0196336 A1 | 7/2017 | Smal | |
| 2020/0104998 A1* | 4/2020 | Dacosta | A61B 5/0077 |
| 2021/0220665 A1* | 7/2021 | Ruiz | A61B 5/0059 |
| 2023/0149077 A1* | 5/2023 | Van Gool | A61B 5/6898 |
| | | | 606/9 |
| 2024/0081624 A1* | 3/2024 | Yu | A61B 1/00052 |

FOREIGN PATENT DOCUMENTS

| | | |
|---|---|---|
| WO | 2004007022 A1 | 1/2004 |
| WO | 2016014132 A1 | 1/2016 |
| WO | 2018167073 A1 | 9/2019 |

* cited by examiner

PERSONAL CARE DEVICE CONFIGURED TO PERFORM A LIGHT-BASED HAIR REMOVAL

CROSS-REFERENCE TO PRIOR APPLICATIONS

This application is the U.S. National Phase application under 35 U.S.C. § 371 of International Application No. PCT/EP2021/059613, filed on Apr. 14, 2021, which claims the benefit of European Patent Application No. 20170690.0, filed on Apr. 21, 2020. These applications are hereby incorporated by reference herein.

FIELD OF THE INVENTION

This disclosure relates to personal care devices configured to perform a light-based hair removal or photo-epilation operation on a body of a subject, and in particular to such personal care devices that can be used with consumer electronic devices, such as smartphones or tablets.

BACKGROUND OF THE INVENTION

Personal care devices exist that can be used to perform a light-based hair removal or photo-epilation operation on a subject, using laser and light therapies known as photo-epilation or Intense Pulsed Light (IPL). Such personal care devices for hair growth reduction may require contact with skin.

Light-based hair removal is a treatment used to inhibit the growth of hair by exposing the skin to bright flashes or pulses of light, which can be referred to as IPL (Intense Pulsed Light) where the light pulse is generated by a lamp or light bulb. Alternatively the flash or pulse can be generated using a laser or one or more light emitting diodes (LEDs). The light penetrates the skin and is absorbed—among other places—in the root of the hair. The temperature of the root of the hair will rise and subsequently the temperature of the surrounding tissue will also rise. The growth of the hair is inhibited if the temperature rise is sufficient. This process is known as photothermolysis.

A personal care device for light-based hair removal may include one or more sensors for monitoring one or more parameters before or during a light-based hair removal operation. For example, contact with skin is required for successful photo-epilation treatment and to prevent a light pulse being directed into other body parts such as eyes, which can result in injury. Therefore the personal care device may include a skin contact sensor for measuring or detecting contact with the skin. Another type of sensor used in personal care devices for light-based hair removal is a skin tone sensor that measures the tone of the skin that a light-based hair removal operation (photo-epilation) is to be applied to.

It has been realised that including these (and other) different sensors in a personal care device for light-based hair removal can increase the cost and complexity of such devices (including the manufacture of these devices), and it is desirable to provide a personal care device for light-based hair removal with these functions without substantially increasing the cost and/or complexity of the personal care device.

SUMMARY OF THE INVENTION

It has been realised that smartphones and other types of consumer electronic devices (such as laptops, tablets, etc.) include a number of different types of sensors that can be used to obtain information useful for a light-based hair removal operation. In particular, many types of consumer electronic devices include one or more cameras or imaging units that can be used to obtain images of the subject, with those images processed to determine one or more parameters useful for the light-based hair removal operation.

In some cases, these images are required in real-time, i.e. they are required at the time that the light-based hair removal operation is to be performed. For example, image(s) may need to be available at the time that a light pulse is to be triggered so that it can be determined whether the personal care device is in contact with the skin, and/or that the tone of the skin is appropriate for the light pulse to be generated. A smartphone or other consumer electronic device would typically have to be manually held by the user of the personal care device or otherwise positioned in the environment of the subject in an appropriate position to obtain the required images, which can be difficult when the user also has to manually hold the personal care device.

Therefore, it is desirable to provide solutions to one or more of the above problems that enables a smartphone or other similar type of consumer electronic device to be used more easily with a personal care device for light-based hair removal or photo-epilation.

According to a first specific aspect, there is provided a personal care device configured to perform a light-based hair removal or photo-epilation operation on a body of a subject. The personal care device comprises a housing including a first window or opening; a light source configured to generate light to perform the light-based hair removal or photo-epilation operation, wherein the light source is arranged in the housing such that light emitted by the light source illuminates a part of the body; a receiving member provided in or on the housing configured to receive and retain a consumer electronic device in or on the personal care device; and an optical system in the housing configured to enable an imaging unit of the consumer electronic device when retained by the receiving member to obtain images of a part of the body via the first window or opening.

In some embodiments, the optical system comprises one or more mirrors and/or lenses.

In some embodiments, the optical system is adjustable to accommodate different positions of imaging units of different types of consumer electronic devices.

In some embodiments, the optical system is configured to be adjustable in at least one of a direction perpendicular to a plane of the first window or opening and a direction parallel to a plane of the first window or opening.

In some embodiments, the optical system is configured to enable light from a light source of the consumer electronic device to pass through the first window or opening.

In some embodiments, the receiving member is configured such that the consumer electronic device is received and retained in or on the personal care device so that an imaging plane of the imaging unit of the consumer electronic device is perpendicular or substantially perpendicular to a plane of the first window or the opening.

In some embodiments, the receiving member comprises a recess provided in the housing and configured and shaped to receive the consumer electronic device in an at least partially submerged position in the housing.

In some embodiments, the recess is shaped to enable consumer electronic devices having different sizes to be received and retained in the recess.

In some embodiments, the personal care device further comprises a retaining mechanism configured to retain the consumer electronic device in the recess in a stationary position relative to the housing.

In some embodiments, the retaining mechanism is configured to retain consumer electronic devices having different sizes in the recess. In these embodiments, the retaining mechanism can comprise a cover plate that is configured to be placed over a part of the consumer electronic device when received in the recess to thereby retain the consumer electronic device in or on the personal care device. In alternative embodiments, the retaining mechanism can comprise a plurality of cover plates, wherein each cover plate is configured to be placed over a part of a consumer electronic device having a respective size when received in the recess, wherein each cover plate is configured to retain the consumer electronic device having the respective size in or on the personal care device.

In some embodiments, the personal care device is configured to perform the light-based hair removal or photo-epilation operation on a part of the body adjacent to the first window or opening. In alternative embodiments, the personal care device further comprises an aperture, and the personal care device is configured to perform the light-based hair removal or photo-epilation operation on a part of the body adjacent to the aperture.

In some embodiments, the personal care device further comprises interface circuitry in the housing configured to communicate with the consumer electronic device. In these embodiments, the interface circuitry can be configured to communicate wirelessly with the consumer electronic device.

In some embodiments, the personal care device further comprises wireless charging circuitry located adjacent to the recess configured to enable wireless charging of the consumer electronic device.

In some embodiments, the personal care device further comprises control circuitry in the housing configured to control one or more operations of the personal care device.

In some embodiments, the control circuitry is configured to control operation(s) of the personal care device in response to, or based on, information received from the consumer electronic device. In these embodiments, the information can comprise one or more images obtained by the imaging unit of the consumer electronic device via the optical system, and/or the information is derived from one or more images obtained by the imaging unit of the consumer electronic device via the optical system. In these embodiments, the information can relate to any of: skin tone, whether the personal care device is in contact with a part of the body of the subject, presence of hairs and/or other skin features, and feedback on the light-based hair removal or photo-epilation operation.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF THE EMBODIMENTS

Figure 1:
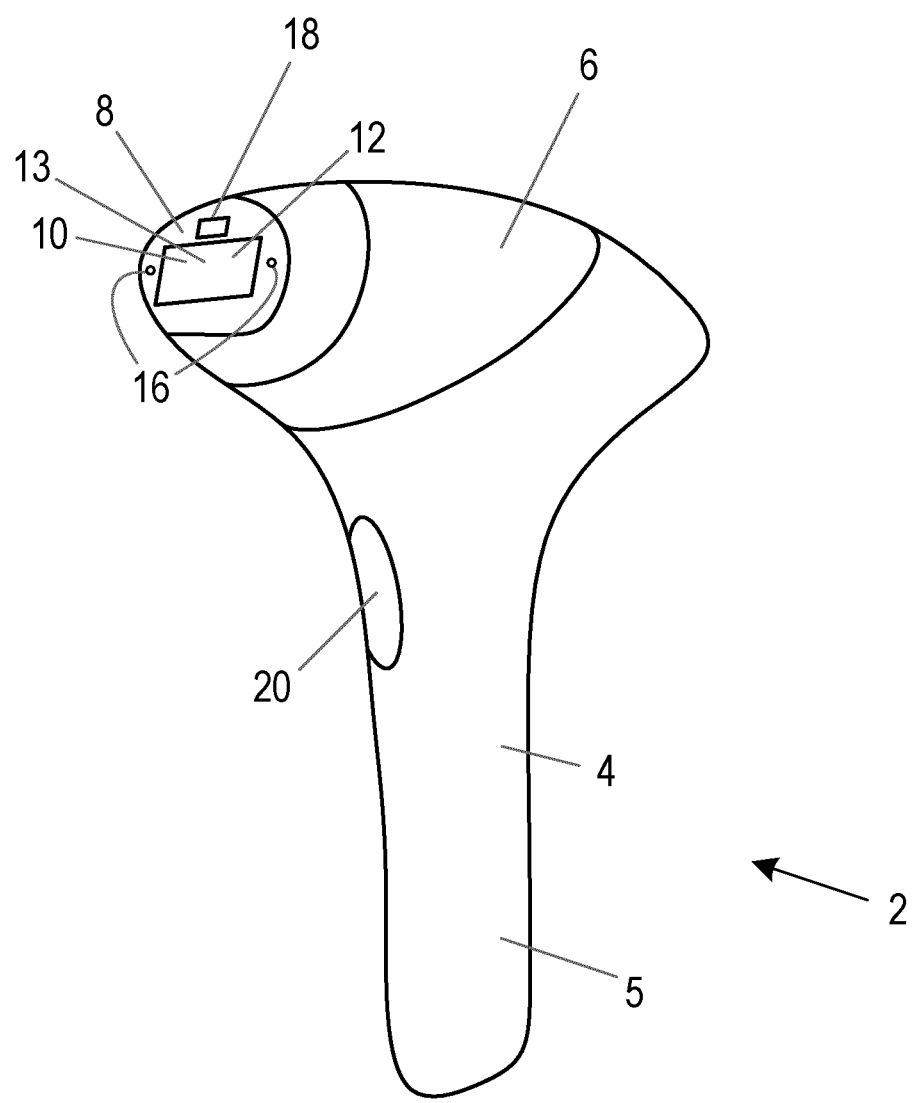
FIG. 1 is an illustration of a conventional light-based personal care device for light-based hair removal or photo-epilation.

FIG. 1 is an illustration of a conventional personal care device 2 that can be used to perform a light-based hair removal or photo-epilation operation involving the application of a light pulse to an area of skin. The personal care device 2 can be held in one or both hands of a user during use. The personal care device 2 is for use on a body of a subject (e.g. a person or an animal) and is to perform a light-based hair removal or photo-epilation operation on the body of the subject when the personal care device 2 is in contact with skin of the subject, known as photo-epilation or Intense Pulsed Light (IPL) hair growth reduction.

As described herein, a personal care device 2 is operated or used by a 'user', and the personal care device 2 is used on a body of a 'subject'. In some cases the user and the subject is the same person, i.e. the personal care device 2 is held in a hand and used by a user on themselves (e.g. used on the skin on their leg). In other cases the user and the subject are different people, e.g. the personal care device 2 is held in a hand and used by a user on someone else.

The personal care device 2 comprises a housing 4 that includes at least a handle portion 5 and a main body portion 6. The handle portion 5 is shaped to enable the user to hold the personal care device 2 with one hand. The main body portion 6 has a first end 8 that is to be placed into contact with the skin of the subject when the light-based hair removal or photo-epilation operation is to be performed on the body or skin of the subject.

In FIG. 1, the personal care device 2 is configured to perform a light-based hair removal or photo-epilation operation using light or light pulses. Thus, in FIG. 1 the first end 8 comprises an aperture 10 arranged in or on the first end 8 of the main body portion 6 so that the aperture 10 can be placed adjacent to or on (i.e. in contact with) the skin of the subject. The personal care device 2 includes one or more light sources 12 that are configured to generate light pulses that are to be applied to the skin of the subject via the aperture 10 and effect a light-based hair removal or photo-epilation operation. The one or more light sources 12 are arranged in the housing 4 (e.g. in the main body portion 6) so that the light pulses are provided from the one or more light sources 12 through the aperture 10. The aperture 10 may be in the form of an opening at the first end 8 of the housing 4, and may include an optical waveguide 13 that is transparent or semi-transparent to the light pulses (i.e. the light pulses can pass through the optical waveguide 13).

In FIG. 1, the aperture 10 and optical waveguide 13 have a generally rectangular shape, which results in a generally rectangular-shaped region on the skin on which the light-based hair removal operation is performed. It will be appreciated that the aperture 10 and/or optical waveguide 13 can have any other desired shape. For example the aperture 10 and/or optical waveguide 13 can be square, elliptical, circular, or any other polygonal shape.

The light source 12 can be configured to generate a light pulse at any suitable or desired wavelength (or range of wavelengths) and/or intensities. For example, the light source 12 can generate visible light, infra-red (IR) light and/or ultraviolet (UV) light. Each light source 12 can comprise any suitable type of light source, such as one or more light emitting diodes (LEDs), a flash lamp (e.g. a Xenon flash lamp), a laser or lasers, etc. In a preferred embodiment, the personal care device 2 is configured to perform photo-epilation, and the light source(s) 12 are to provide intense light pulses. For example the light source(s) 12 can provide light pulses with spectral content in the 560-1200 nanometre (nm) range for a duration of around 2.5 milliseconds (ms), as these wavelengths heat melanin in the hair and hair root by absorption, which puts the hair follicles in a resting phase, preventing hair regrowth.

The one or more light sources 12 are configured to provide pulses of light. That is, the light source(s) 12 are configured to generate light at a high intensity for a short duration (e.g. less than 1 second). The intensity of the light pulse should be high enough to effect the light-based hair removal or photo-epilation operation on the skin or body part adjacent the aperture 10.

The illustrated hand-held device 2 also includes two skin contact sensors 16 positioned on or in the first end 8 that are used to determine when the first end 8 is in contact with the skin. The skin contact sensors 16 measure a parameter that is indicative of whether the first end 8 is in contact with skin, and generate respective measurement signals (referred to as 'skin contact measurement signals') that comprise a time-series of measurements of the parameter. Typically a skin contact sensor is used in a personal care device 2, particularly a photo-epilator, to make sure that the personal care device 2 is correctly in contact with skin before a light pulse is generated to avoid the light pulse being directed into the eyes of the user or subject.

The parameter can be capacitance, and so the skin contact sensors 16 can measure capacitance via a respective pair of electrical contacts or electrodes on the surface of the first end 8, with the measured capacitance being indicative of whether there is skin contact. Alternatively, the parameter can be an intensity or level of light, and so the skin contact sensors 16 can be light sensors that measure an intensity or level of light incident on the light sensor, with the measured intensity or level being indicative of whether there is skin contact (e.g. less/no light could indicate skin contact as the skin obscures the light sensors 16, and vice versa). In other alternatives, the parameter can be a measure of contact pressure, and so the skin contact sensors 16 can measure contact pressure via respective pressure sensors or mechanical switches, with the measured contact pressure being indicative of whether there is skin contact.

The illustrated personal care device 2 also includes a skin tone sensor 18 positioned on or in the first end 8 that is used to determine a skin tone of the skin that the first end 8 is in contact with. The skin tone sensor 18 measures a parameter that is indicative of the skin tone of the skin, and generates a measurement signal (referred to as a 'skin tone measurement signal') that comprises a time-series of measurements of the parameter. Typically a skin tone sensor is used in a personal care device 2, particularly a photo-epilator, to make sure that the light pulse has an intensity that is appropriate for the type of skin being treated, or even to prevent a light pulse being generated if the skin type is unsuitable for light pulses (e.g. darker skin which has a much higher melanin content).

The skin tone sensor 18 can be a light sensor and the parameter measured by the light sensor can be an intensity or level of light at a particular wavelength or multiple wavelengths reflected from the skin. The measured intensity or level of reflected light at a particular wavelength(s) can be indicative of the skin tone. The measured intensity or level of reflected light can be based on the concentration of melanin in the skin, and thus the measured intensity or level can indicate the melanin concentration. The melanin concentration can be derived, for example, from measurements of light reflection at 660 nm (red) and 880 nm (infrared) wavelengths.

The illustrated personal care device 2 also includes a user control 20 that can be operated by the user to activate the personal care device 2 so that the required light-based hair removal or photo-epilation operation is performed on the body of the subject (i.e. me generation of a light pulse by the one or more light source(s) 12). The user control 20 may be in the form of a switch, a button, a touch pad, etc.

As noted above, personal care devices can have several types of sensors for monitoring one or more parameters before or during a light-based hair removal or photo-epilation operation, such as skin contact sensors 16 and skin tone sensor 18. It is desirable to incorporate one or more cameras or imaging units into personal care devices, as these cameras/imaging units can be used to obtain images of the subject, with those images processed to determine one or more parameters useful for the light-based hair removal or photo-epilation operation, such as whether there is skin contact, the skin tone, determining progress/success of a light-based hair removal or photo-epilation operation and/or determining a target area on the skin for the light-based hair removal or photo-epilation operation.

Including a camera/imaging unit in a personal care device is likely to increase the cost and complexity of such devices (including the manufacture of these devices), and so efforts have been made to make use of cameras or imaging units within smartphones or other types of consumer electronic devices, such as a tablets, smartwatches, laptops, etc. However, a smartphone or other consumer electronic device would typically need to be manually held by the user of the personal care device in an appropriate position to obtain the required images, which can be difficult when the user also has to manually hold the personal care device.

The present disclosure addresses these problems, and enables a smartphone or other consumer electronic device to be received and retained in or on the personal care device so that an imaging unit of the consumer electronic device is able to obtain images of a part of the body via a first window or opening in the housing of the personal care device. In particular, a receiving member is provided in or on the housing of the personal care device, and the receiving member is configured to receive and retain a consumer electronic device in or on the personal care device. In some embodiments, the receiving member is or includes a recess so that the consumer electronic device is at least partially submerged below the outer surface of the housing, but in other embodiments the receiving member enables the consumer electronic device to be retained on the outer surface of the housing of the personal care device.

Figure 2:
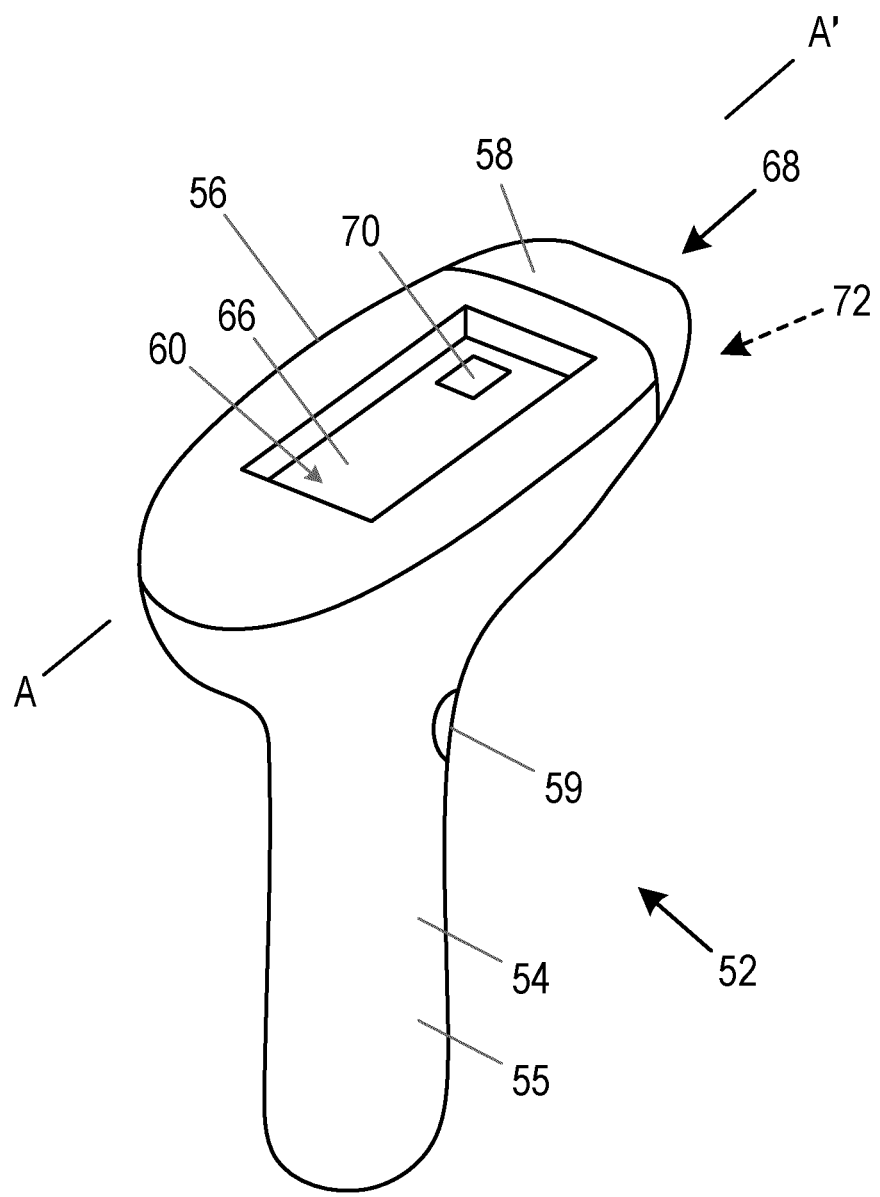
FIG. 2 is an illustration of a personal care device according to an exemplary embodiment having a recess for receiving and retaining a consumer electronic device in the form of a smartphone.

FIG. 2 is an illustration of a personal care device 52 according to an exemplary embodiment having a receiving member in the form of a recess for receiving and retaining a consumer electronic device in the form of a smartphone.

The personal care device 52 can be held in one or both hands of a user during use. The personal care device 52 is for use on a body of a subject (e.g. a person or an animal) and is to perform a light-based hair removal or photo-epilation operation on the body of the subject when the personal care device 52 is in contact with skin of the subject (photo-epilation or IPL), including hair growth reduction.

The personal care device 52 comprises a housing 54 that includes at least a handle portion 55 and a main body portion 56. The handle portion 55 is shaped to enable the user to hold the personal care device 52 with one hand or both hands. The main body portion 56 has a first end 58 (also referred to herein as the 'front end 58') that is to be placed into contact with the skin of the subject when the light-based hair removal or photo-epilation operation is to be performed on the body or skin of the subject.

The personal care device 52 comprises suitable components for performing the light-based hair removal or photo-epilation operation. Similar to the personal care device 2 shown in FIG. 1, the personal care device 52 is configured to perform a light-based hair removal or photo-epilation operation using light or light pulses, and so the personal care device 52 comprises one or more light sources that are configured to generate light pulses that are to be applied to the skin of the subject. The one or more light sources can be arranged in the housing 54 (e.g. in the main body portion 56) so that light pulses generated by the one or more light sources are emitted towards the skin from the first end 58.

The personal care device 52 can comprise a user control 59 that can be operated by the user to activate the personal care device 52 so that the required light-based hair removal or photo-epilation operation is performed on the body of the subject (i.e. the generation of a light pulse by one or more light sources). The user control 59 may be in the form of a switch, a button, a touch pad, etc.

The housing 54, and in this example the main body portion 56, includes a receiving member 60 in the form of a recess that is configured to receive and retain a consumer electronic device in or on the personal care device 52. The recess 60 is therefore shaped to receive at least part, or all, of a consumer electronic device 62 and hold (retain) it in or on the personal care device 52, so that the consumer electronic device is effectively integral to (and moves with) the personal care device 52. Thus the recess is configured and shaped to receive the consumer electronic device 62 in an at least partially submerged position in the housing 54.

It is intended that any typically available consumer electronic device that has one or more imaging units can be used with the personal care device 52, and so the receiving member 60 is shaped or sized large enough to accommodate typically available consumer electronic devices. Typically, suitable consumer electronic devices, such as smartphones and tablets, are generally rectangular (cuboid) in shape, and so the recess 60 may have a rectangular opening to enable is generally rectangular-shaped consumer electronic devices to be received in the recess 60. The recess 60 may be deep enough for an upper surface of the consumer electronic device to be generally level (i.e. generally flush) with the outer surface of the housing 54, or the upper surface of the consumer electronic device may be above the outer surface of the housing 54 (i.e. partially submerged) or below the outer surface of the housing 54 (i.e. fully submerged).

Those skilled in the art will appreciate that the shape and/or size of the recess 60 can be different to that shown in FIG. 2 to enable a wider or narrower range different-sized consumer electronic devices to be used with the personal care device 52.

Figure 3:
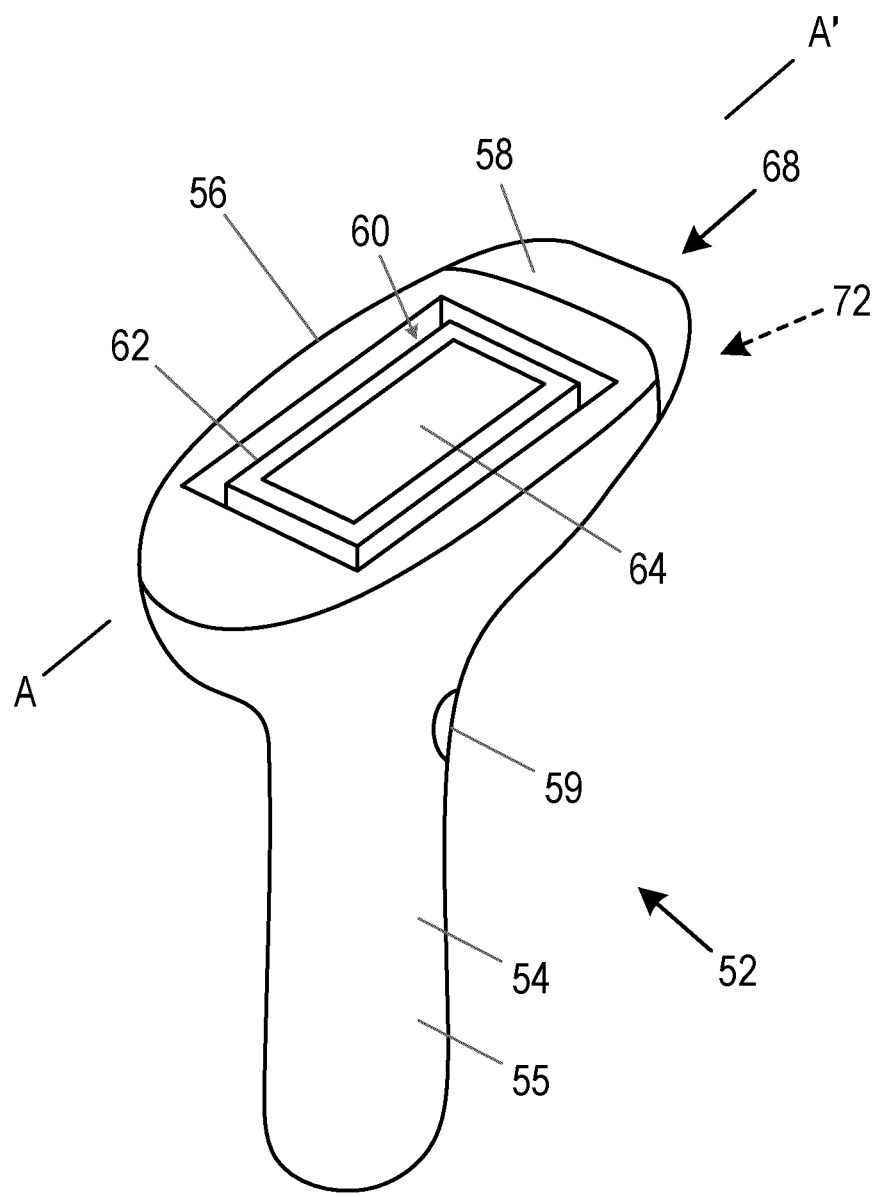
FIG. 3 is an illustration of a personal care device according to an exemplary embodiment having a consumer electronic device in the form of a smartphone retained therein.

FIG. 3 shows the personal care device 52 of FIG. 2 with a consumer electronic device 62 in the form of a smartphone or tablet 62 retained in the recess 60. The consumer electronic device 62 has a display screen 64 that is used to display information relating to the operation of the consumer electronic device 62. The display screen 64 is on an upper surface of the consumer electronic device 62. The display screen 64 may be a touchscreen that can be used to provide inputs to the consumer electronic device 62.

A consumer electronic device 62 typically comprises one or more imaging units arranged on the opposite side of the consumer electronic device 62 to the display screen 64, i.e. the imaging unit(s) are arranged on the side of the consumer electronic device 62 that faces towards the bottom surface 66 of the recess 60. This side is referred to herein as the 'lower side' of the consumer electronic device 62.

As noted above, the imaging unit(s) arranged on the lower side of the consumer electronic device 62 are to be used to obtain images of a part of the body on which a light-based hair removal or photo-epilation operation may be, or has, been performed. Therefore it is required for the imaging unit(s) of the consumer electronic device 62 to be able to obtain images via the housing 54 of the personal care device 52.

To enable the image(s) to be obtained, the housing 54 comprises a first window or opening 68 in the front end 58 of the personal care device 52, and a second window or opening 70 in the bottom surface 66 of the recess 60. The first window or opening 68 is not visible in FIG. 2 or 3, but, for example, the first window or opening 68 can be positioned on the first end 58 at a similar position to the skin tone sensor 18 in the conventional device shown in FIG. 1. In embodiments where the first window or opening 68 and/or the second window or opening 70 is a window, the first window 68 and/or the second window 70 may comprise a translucent or transparent material, for example formed from glass or plastic. In embodiments where the first window or opening 68 and/or the second window or opening 70 is an opening, no material (such as glass or plastic) may cover the opening. As imaging units of consumer electronic devices can often protrude from the back surface of the consumer electronic device (e.g. due to the presence of one or more lens arrangements, etc.), it can be beneficial for the second window or opening 70 to be an opening to accommodate the protruding imaging unit. The first window or opening 68 and the second window or opening 70 are linked by an optical system within the housing 54 (also not visible in FIG. 2 or 3) that enables the imaging unit(s) to observe (and obtain images of) skin adjacent to or in contact with the first window or opening 68.

As the position of an imaging unit on a lower side of a consumer electronic device 62 is not standardised, the second window or opening 70 can be relatively large to allow for different possible positions of an imaging unit. In some embodiments, to accommodate all possible positions of an imaging unit on a consumer electronic device 62, the second window or opening 70 can be approximately the size of the consumer electronic device 62. Although the second window or opening 70 is shown as being generally square, it will be appreciated that the second window or opening 70 may have different shapes to that shown. For example, the second window or opening 70 can be rectangular, elliptical, circular, or any other polygonal shape.

It will be appreciated that in embodiments where the receiving member 60 is not a recess (i.e. the consumer electronic device 62 is to be retained on or close to (i.e. at a relatively small distance from) the surface of the housing 54), the housing 54 comprises the second window or opening 70 in the surface of the housing 54.

Similar to the personal care device 2 shown in FIG. 1, the personal care device 52 shown in FIGS. 2 and 3 is configured to perform a light-based hair removal or photo-epilation operation using light or light pulses, and so the first end 8 may comprise an aperture 72 arranged in or on the first end 58 of the main body portion 56 so that the aperture 72 can be placed adjacent to or on (i.e. in contact with) the skin of the subject. The personal care device 52 includes one or more light sources (not shown) that are configured to generate light pulses that are to be applied to the skin of the subject via the aperture 72 and effect a light-based hair removal or photo-epilation operation. The one or more light sources are arranged in the housing 54 (e.g. in the main body portion 56) so that the light pulses are provided from the one or more light sources through the aperture 72. The aperture 72 may be in the form of an opening or window at the first end 58 of the housing 54, and may include an optical waveguide that is transparent or semi-transparent to the light pulses (i.e. the light pulses can pass through the optical waveguide).

In some embodiments, the aperture 72 and the first window or opening 68 are separate, which means that the imaging unit(s) of the consumer electronic device 62 obtain image(s) via a different window/opening through which the light or light pulse(s) are applied. In this case, the images obtained may be of skin that is adjacent or directly adjacent to an area of skin that the light-based hair removal or photo-epilation operation will be performed on in the current position of the personal care device 52.

In alternative embodiments, the aperture 72 is the first window or opening 68, which means that the imaging unit(s) of the consumer electronic device 62 obtain image(s) via the same window/opening through which the light or light pulse(s) are applied. In these embodiments, the optical system may be such that the imaging unit(s) obtain image(s) via a first part of the first window or opening 68, and the light or light pulse(s) are applied to the skin via a second (different) part of the first window or opening 68. Alternatively, the optical system may be such that the imaging unit(s) obtain image(s) and the light or light pulse(s) are applied to the skin generally via the first window or opening 68 or the same part of the first window or opening 68, which means that the imaging unit is able to obtain images of the same part of the skin to which the light or light pulse(s) are applied. More generally, in these embodiments the light-based hair removal or photo-epilation operation can be performed on a part of the body through or via the first window or opening 68, and the imaging unit(s) of the consumer electronic device 62 can obtain image(s) via the same window/opening. This enables images to be obtained of the same part of the skin to which the light-based hair removal or photo-epilation operation is to be applied.

In some embodiments, the first window 68 and/or the aperture 72 (if present) have a generally rectangular shape, which results in a generally rectangular-shaped region on the skin that can be observed by the imaging unit and/or on which the light-based hair removal or photo-epilation operation is performed. It will be appreciated that the first window 68 and/or aperture 72 can have any other desired shape. For example the first window 68 and/or aperture 72 can be square, elliptical, circular, or any other polygonal shape.

Figure 4:
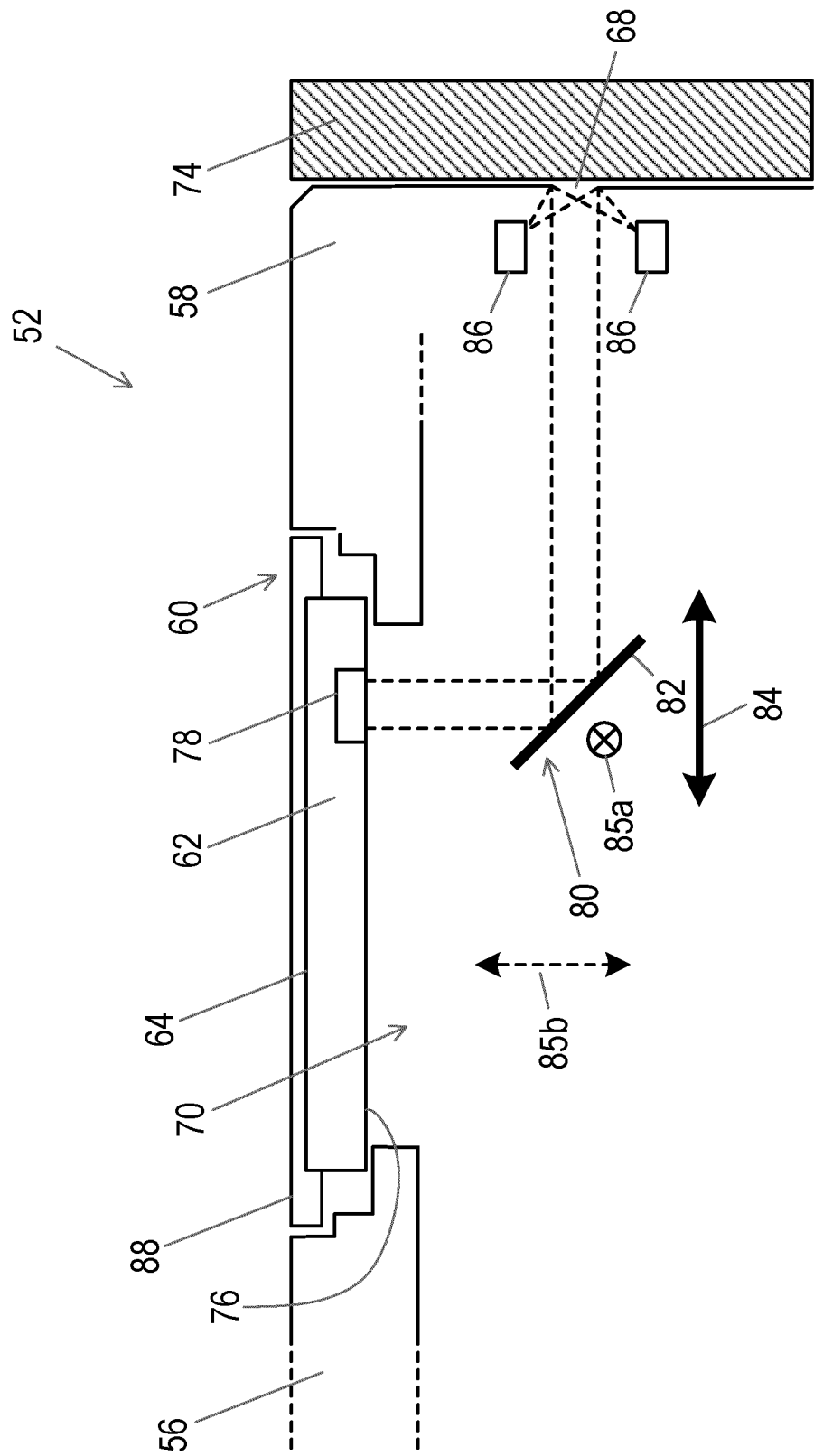
FIG. 4 is a cutaway view of a personal care device according to an exemplary embodiment having a consumer electronic device in the form of a smartphone retained therein.

FIG. 4 is a cutaway view of a personal care device 52 and retained consumer electronic device 62 of FIG. 3 along part of line A-A' in FIGS. 2 and 3. Although the personal care device 52 in FIG. 4 is not completely identical to the personal care device 52 shown in FIGS. 2 and 3, like components and features have been given the same reference numeral, and the description of the personal care device 52 above applies also to the personal care device 52 in FIG. 4. In this embodiment, the second window or opening 70 is an opening, but it will be appreciated that it can be a window instead (e.g. comprising a transparent or translucent material).

Thus, FIG. 4 shows consumer electronic device 62 retained by the receiving member 60, and also shows the first window or opening 68 (in the form of an opening) at the first end 58 of the personal care device 52. The personal care device 52 is shown next to an area of skin 74 that the personal care device 52 can perform the light-based hair removal or photo-epilation operation on. FIG. 4 shows the lower side 76 of the consumer electronic device 62, and the imaging unit 78 of the consumer electronic device 62. Although in this embodiment the first window or opening 68 is shown as an opening, it will be appreciated that it can be a window instead (e.g. comprising a transparent or translucent material). Moreover, it will be appreciated that although this embodiment is shown as having a receiving member in the form of a recess 60, the receiving member can alternatively retain the consumer electronic device 62 on the surface of the housing 54, and the second window or opening 70 will be a window or opening in the surface of the housing 54.

The second window or opening 70 shown in FIG. 4 is relatively larger than that shown in FIG. 2, which enables the personal care device 52 to be used with consumer electronic devices with a wider range of positions for the imaging unit 78.

The optical system 80 is shown within the housing 54 that links the first window or opening 68 and the second window or opening 70, and that is configured to enable the imaging unit 78 to observe (and obtain images of) the skin 74 adjacent to or in contact with the first window or opening 68. In the illustrated embodiment, the optical system 80 comprises at least one mirror 82 arranged and oriented so that the imaging unit 78 can observe the area of skin 74. As the plane of the consumer electronic device 62 and also the imaging plane of the imaging unit 78 is generally perpendicular to the plane of the first window or opening 68 (or perpendicular to the plane of the skin 74 at the first window or opening 68), the plane of the mirror 82 is oriented at an angle of approximately 45° with respect to the consumer electronic device 62 and the first window or opening 68. Ii will De appreciated that the optical system 80 shown in FIG. 4 is quite simple, but those skilled in the art will appreciate that more complex optical systems can be used (for example comprising multiple mirrors and/or other optical components such as lenses and prisms).

As the particular position of the imaging unit 78 on the lower side 76 of a consumer electronic device 62 is consumer electronic device-specific (i.e. varies between models and devices), there may not be a single position or location of the mirror 82 (or more generally the optical system 80) that enables the imaging unit 78 of any given consumer electronic device 62 to observe the area of skin 74 through the first window or opening 68. Therefore, in some embodiments the optical system 80 is adjustable to accommodate different positions of imaging units 78 on different types of consumer electronic devices 62. For example, as indicated by arrow 84, the mirror 82 in the optical system 80 can be configured to be adjustable in a direction perpendicular to a plane of the first window or opening 68 (i.e. towards or away from the first window or opening 68). In another or further example, the mirror 82 in the optical system 80 can be configured to be adjustable in a direction parallel to a plane of the first window or opening 68 (i.e. laterally with respect to the first window or opening 68). This is illustrated by arrows 85*a* and 85*b*. The optical system 80 may therefore comprise one or more guides or rails along which the mirror 82 or other optical components can be moved. The optical system 80 may be adjustable manually by the user, for example by the user effecting the adjustment using one or more user interface components (e.g. a switch, a dial, a control shown on a touchscreen of the consumer electronic device 62, etc.), or the optical system 80 may be adjusted automatically by the personal care device 52 or the consumer electronic device 62, for example by actuating one or more motors or other actuator to move the optical system 80 (or one or more optical components thereof) to the appropriate position. Such a mechanism may have a similar mechanism to an autofocus and/or zoom arrangement in a conventional digital camera.

In some embodiments, the optical system 80 can comprise one or more lenses configured to enable or assist the imaging unit 78 to obtain a suitable focussed image of the skin 74.

When the first window or opening 68 is positioned against the skin 74, it may be difficult for the imaging unit 78 to obtain a good image of the skin 74 due to low light conditions. Therefore, in some embodiments, the optical system 80 is such that a flash component of the consumer electronic device 62, or other light source component of the consumer electronic device 62, is able to illuminate the skin 74 adjacent to the first window or opening 68 when the imaging unit 78 is to obtain an image of the skin 74.

In alternative embodiments, the personal care device 2 may include one or more light sources 86 that are used to illuminate the skin 74 adjacent to the first window or opening 68 when the imaging unit 78 is to obtain images. In FIG. 4 two light sources 86 are shown, arranged close to the first window or opening 68. The light sources 86 may be light emitting diodes (LEDs), incandescent lamps, halogen lamps, etc. Typically the light source(s) 86 is/are different light sources to any light source used to effect a light-based hair removal operation (such as photo-epilation), although in some embodiments the light source used to effect the light-based hair removal operation can be used to illuminate the skin 74 when images are to be obtained.

As noted above, the recess 60 is shaped to receive at least part, or all, of a consumer electronic device 62 and hold (retain) it in or on the personal care device 52. The recess 60 may be shaped or configured to hold the consumer electronic device 62 in place once it has been received in the recess 60. For example, at least a part of the walls of the recess 60 may be shaped or gradually tapered in so that the consumer electronic device 62 can be held by friction with the walls of the recess 60. In alternative embodiments, the recess 60 or the personal care device 52 more generally may comprise a retaining mechanism that enables consumer electronic devices 62 of different sizes to be retained in the recess 60. The retaining mechanism may be configured to retain the consumer electronic device 62 in the recess 60 in a stationary position relative to the housing 54. Some examples of suitable retaining mechanisms include one or more straps, a hook-and-loop based retaining system, one or more protrusions (for enabling a friction fit), one or more clips, one or more clamps, etc. Likewise, in embodiments where the receiving member 60 retains the consumer electronic device 62 on or close to the surface of the housing 54, the receiving member 60 can be shaped or configured to hold the consumer electronic device 62 in place once it has been received on or close to the surface. The receiving member may comprise a retaining mechanism that enables consumer electronic devices 62 of different sizes to be retained by the receiving member in a stationary position relative to the housing 54. Some examples of suitable retaining mechanisms include one or more straps, a hook-and-loop based retaining system, one or more protrusions (for enabling a friction fit), one or more clips, one or more clamps, etc.

FIG. 4 shows another embodiment of a retaining mechanism in the form of a cover plate 88 that can be moved or removed to enable a consumer electronic device 62 to be placed into the recess 60, and then moved or replaced over at least part of the consumer electronic device 62 to retain the consumer electronic device 62 in or on the personal care device 52. The cover plate 88 may be shaped so that it only substantially covers a border or bezel portion of the consumer electronic device 62, i.e. a portion of the consumer electronic device 62 around the display screen 64. Alternatively (and this may depend on the size of the consumer electronic device 62), the cover plate 88 may cover a part or all of the display screen 64. The cover plate 88 may be formed of any suitable material or combination of materials, such as metal, plastic, etc.

In some embodiments, in view of the different sizes of consumer electronic devices 62 that can be received in the recess 60, there may be different cover plates 88 that are suitable for different types and/or different sizes of consumer electronic device 62. Thus, when a consumer electronic device 62 is placed into the recess 60, a suitable cover plate 88 from the set of cover plates 88 is selected to retain the consumer electronic device 62 in place.

Figure 5:
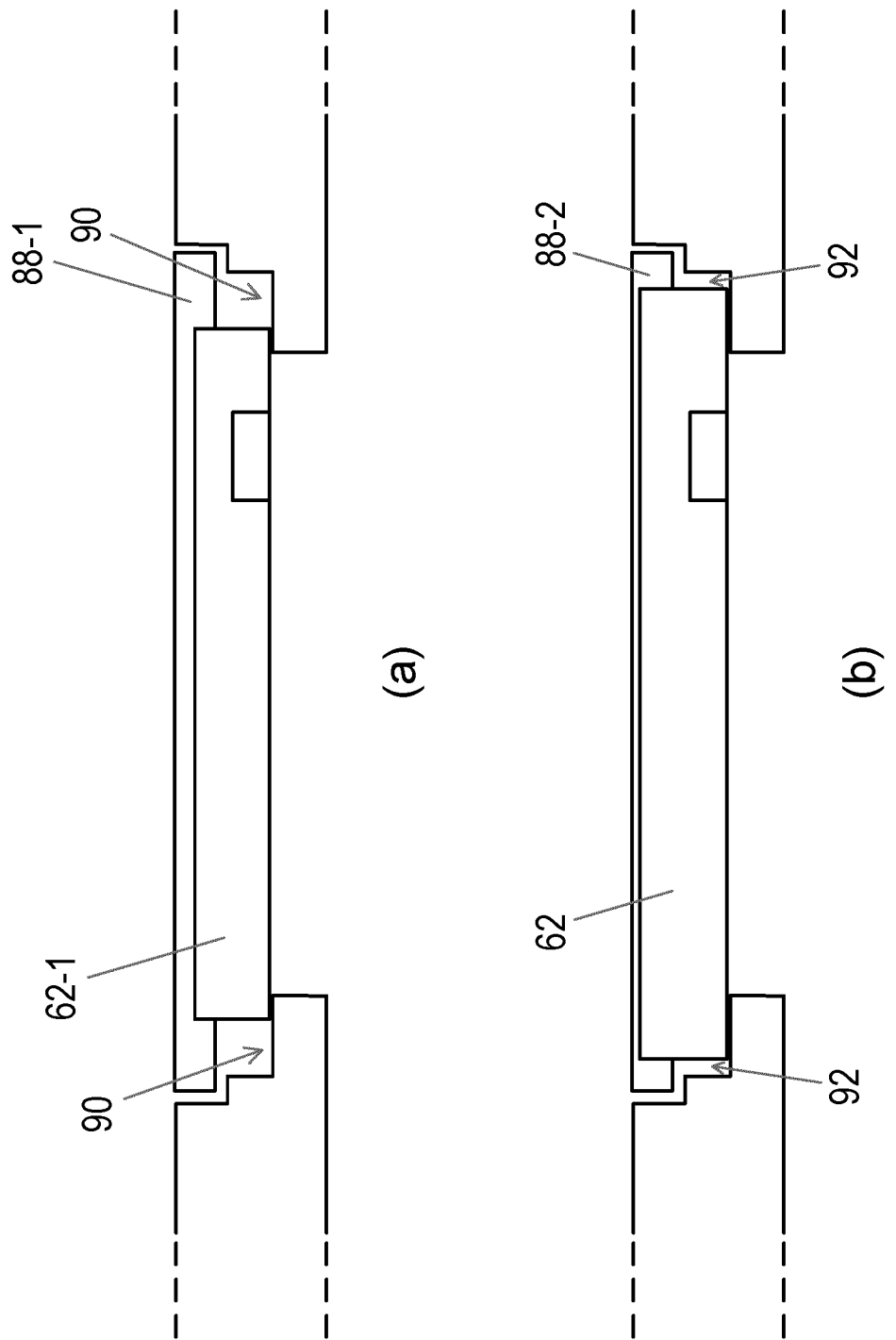
FIGS. 5(a) and (b) are cutaway views of part of a personal care device according to an exemplary embodiment having different sized cover plates.

FIGS. 5(*a*) and (*b*) are cutaway views of part of a personal care device 52 showing the use of different sized cover plates 88. In FIG. 5 the personal care device 52 generally corresponds to the personal care device 52 shown in FIGS. 3 and 4. In FIG. 5(*a*) the consumer electronic device 62-1 is relatively small, and there are gaps 90 between the edge of the consumer electronic device 62-1 and the walls of the recess 60. Therefore, the cover plate 88-1 used in this case is shaped to hold the smaller-sized consumer electronic device 90-1 in place in the recess 60. In FIG. 5(*b*) the consumer electronic device 62-2 is larger, and mostly fills the recess 60 (i.e. there are only small gaps 92 between the edge of the consumer electronic device 62-2 and the walls of the recess 60). Therefore, the cover plate 88-2 used in this case is shaped to hold the larger-sized consumer electronic device 90-2 in place in the recess 60. Moreover, as the larger-sized consumer electronic device 62-2 is thicker, the cover plate 88-2 can be thinner than the cover plate 88-1 to reduce the amount by which the cover plate 88-2 protrudes from the surface of the personal care device 52.

In some embodiments, although not shown in FIGS. 2-5, the personal care device 52 can include control circuitry in the housing 54 for controlling one or more operations of the personal care device 52, such as the performance of the light-based hair-removal or photo-epilation operation. The control circuitry can be implemented in numerous ways, with software and/or hardware, to perform the various functions described herein. In some embodiments, the control circuitry may comprise a processing unit. In some embodiments, the control circuitry can comprise a memory unit that can store data, information and/or signals for use by the control circuitry in controlling the operation or me personal care device 52.

In some embodiments, the control circuitry, or more generally the personal care device 52 includes interface circuitry in the housing 54 configured to enable communications with (at least) the consumer electronic device 62. The interface circuitry is not shown in FIGS. 2-5. The interface circuitry can be configured to enable a data connection to and/or data exchange with other devices, including any one or more of consumer electronic devices 62, servers, databases and sensors. The connection may be direct or indirect (e.g. via the Internet), and thus the interface circuitry can enable a connection between the personal care device 52 and a network (such as the Internet), or directly between the personal care device 52 and the consumer electronic device 62, via any desirable wired or wireless communication protocol. For example, the interface circuitry can operate using WiFi, Bluetooth, Zigbee, or any cellular communication protocol (including but not limited to Global System for Mobile Communications (GSM), Universal Mobile Telecommunications System (UMTS), Long Term Evolution (LTE), LTE-Advanced, etc.). In a particular example, the interface circuitry can enable the personal care device 52 and the consumer electronic device 62 to communicate using a short-range communication protocol, such as WiFi, Bluetooth or Zigbee. In another particular example, in the case of a wired connection, the interface circuitry may include a socket or plug to enable a wired connection with the consumer electronic device 62, such as a USB plug or socket. In the case of a wireless connection, the interface circuitry (and thus personal care device 52) may include one or more suitable antennas for transmitting/receiving over a transmission medium (e.g. the air). The interface circuitry may be part of or connected to the control circuitry to enable information or data received by the interface circuitry to be provided to the control circuitry, and/or information or data from the control circuitry to be transmitted by the interface circuitry.

In some embodiments, certain control functions or control operations of the personal care device 52 (such as modifying settings for the light-based hair removal or photo-epilation operation, actuating the light-based hair removal or photo-epilation operation, etc.) can be performed by the control circuitry. However, in other embodiments, the certain control functions or control operations of the personal care device 52 may be performed by the consumer electronic device 62, for example by the consumer electronic device 62 running a suitable software application (app). The app may provide the user of the personal care device 52 with a suitable user interface on the display screen 64 for adjusting or controlling settings and/or functions of the personal care device 52, and the consumer electronic device 62 can communicate these settings and/or functions to the personal care device 52 via the interface circuitry, and the control circuitry in the personal care device 52 can effect these settings or functions. In this way, the complexity of the control circuitry in the personal care device 52 can be reduced, and instead much of the processing required to operate the personal care device 52 can be performed by the consumer electronic device 62.

In some embodiments, the personal care device 52 may include wireless charging circuitry located adjacent to (and typically beneath) the bottom surface 66 of recess 60. The wireless charging circuitry can be used to enable wireless charging of a wireless charging-enabled consumer electronic device 62 that is received in the recess 60. Alternatively or in addition, the wireless charging circuitry can be used to enable wireless charging of the personal care device 52 by a wireless charging-enabled consumer electronic device 62 retained in the recess 60. In either case, the wireless charging circuitry in the personal care device 52 can comprise one or more coils or similar arrangements that enables a inductive coupling to be achieved with corresponding components in the consumer electronic device 62.

As noted above, the image(s) obtained by the imaging unit 78 can be processed to determine one or more parameters useful for the light-based hair removal or photo-epilation operation, such as whether the personal care device 52 is in contact with skin (and in some cases whether the skin contact is good or good enough for the light-based hair removal or photo-epilation operation to be performed), the skin tone, determining progress/success of a light-based hair removal or photo-epilation operation and/or determining a target area on the skin for the light-based hair removal or photo-epilation operation. The processing of the images can be performed by the consumer electronic device 62, and the results shared with or sent to the personal care device 52, or the images can be shared with or sent to the personal care device 52, and the personal care device 52 can process the images.

Thus, by enabling a consumer electronic device 62 to be received and retained in a personal care device 52 for light-based hair removal or photo-epilation, it is possible to make use of the imaging unit 78 of the consumer electronic device 62, and optionally other sensors and/or functions of the consumer electronic device 62. For example, other sensors and/or functions of the consumer electronic device 62 that can be used by the personal care device 52 include the display screen 64 (including any touchscreen capability of the display screen 64), an ambient light sensor, position and/or orientation sensors (e.g. an accelerometer and/or gyroscope), a satellite positioning system receiver (e.g. GPS), an altimeter/air pressure sensor, processing circuitry (CPU), network connectivity, and a microphone.

In some embodiments, the skin tone sensor 18 included in conventional personal care devices 2 can be omitted, and instead the image(s) from the imaging unit 78 can be processed to determine the skin tone.

In some embodiments, the skin contact sensors 16 included in conventional personal care device 2 can be omitted, and instead the image(s) from the imaging unit 78 can be processed to determine skin contact, and optionally the quality of the skin contact.

In some embodiments, by combining the image(s) from the imaging unit 78 and measurements from a position sensor of the consumer electronic device 62, it may be possible to determine the position of the personal care device 52 relative to the subject or body, and feedback can be given to the user of the personal care device 52 as to where the personal care device 52 should be placed on the skin. This guidance can lead to a more effective light-based hair removal or photo-epilation operation, avoiding missing parts of the skin, which is a significant issue with some types of light-based hair removal or photo-epilation operations where the areas recently treated by light pulses are not visible.

In some embodiments, processing of the image(s) from the imaging unit 78 can be used to check whether the skin on the body is ready for the light-based hair removal or photo-epilation operation to be performed. For example, in the case of photo-epilation, hair should be shaved or waxed before any treatment, and the processing of the images can allow the presence of hairs to be detected.

In some embodiments, processing of the image(s) from the imaging unit 78 and comparison with previously-obtained images of the same part of the body/skin can be used to provide feedback about the progress of the light-based hair removal or photo-epilation operation.

In some embodiments, network connectivity functions of the consumer electronic device 62 can be used to upload the obtained images to a server which could analyse the images and report back to the consumer electronic device 62 and/or the personal care device 52. This can enable more complex image processing algorithms to be used to analyse the images.

In some embodiments, by using the display screen 64/touchscreen of the consumer electronic device 62 as the user interface of the personal care device 52 (with the consumer electronic device 52 executing a suitable app), an improved or enhanced user interface can be provided for the personal care device 52.

In some embodiments, the display screen 64 can be used to show a live view of the skin by displaying the images from the imaging unit 78 as they are obtained. In some embodiments, guidance information for the user, such as arrows, can also be displayed on the display screen 64 or overlaid on the displayed images that indicate how the user should move the personal care device 52 for the next light-based hair removal or photo-epilation operation.

In some embodiments, a microphone of the consumer electronic device 62 and suitable processing of the recorded audio can be used to enable voice control of the personal care device 52.

In some embodiments of photo-epilation operations, measurements by an ambient light sensor in the consumer electronic device 62 can be used to determine if the ambient light levels are suitable for the photo-epilation operation to be performed. For example, performing a photo-epilation operation when it is too sunny should be avoided, as this might influence the accuracy of the skin tone measurement.

In some embodiments of photo-epilation operations, by using a position sensor (e.g. GPS) and/or altitude sensor, automatic triggering of the light pulses can be performed when the personal care device 52 is at an appropriate position on the skin, and/or the triggering of the light pulses can take into account the ambient air pressure (since the amount of available air-cooling and pulse rate are dependent on the ambient pressure).

In some embodiments, as colour reception characteristics of imaging units 78 may differ between consumer electronic devices 62 (including between consumer electronic devices 74 of the same model), it may be important or useful to calibrate the colour performance of the imaging unit 78. This can be done, for example, by obtaining image(s) of a colour calibration card that has areas of different colours, and processing the images to determine an initial colour and intensity calibration. These embodiments are particularly useful where the images are processed to determine the skin tone. Depending on the complexity of the skin tone sensor algorithm, one or more colours and grey-tones can be included on such a calibration card. For example, some conventional personal care devices use a blue LED to detect skin tone, and in that case only a blue calibration would be necessary. If more colours are used in the skin tone detection algorithm, then these colours also need to be calibrated and included on a colour calibration card.

Therefore, there is provided a personal care device for light-based hair removal or photo-epilation that enables a smartphone or other similar type of consumer electronic device to be used more easily with the personal care device, and in particular enables an imaging unit of the consumer electronic device to obtain images of the skin of the subject even when the consumer electronic device is received and retained in the personal care device.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A personal care device configured to perform a light-based hair removal or photo-epilation operation on a body of a subject, the personal care device comprising:
    a housing including a first window or opening;
    a light source configured to generate light to perform the light-based hair removal or photo-epilation operation, wherein the light source is arranged in the housing such that light emitted by the light source illuminates a part of the body;
    a receiving member provided in or on the housing configured to receive and retain a consumer electronic device in or on the personal care device; and
    an optical system in the housing configured to enable an imaging unit of the consumer electronic device when retained by the receiving member to obtain images of a part of the body via the first window or opening.

2. A personal care device as claimed in claim 1, wherein the optical system comprises one or more mirrors and/or lenses.

3. A personal care device as claimed in claim 1, wherein the optical system (80) is adjustable to accommodate different positions of imaging units of different types of consumer electronic devices.

4. A personal care device as claimed in claim 1, wherein the optical system is configured to be adjustable in at least one of a direction perpendicular to a plane of the first window or opening and a direction parallel to a plane of the first window or opening.

5. A personal care device as claimed in claim 1, wherein the optical system is configured to enable light from a light source of the consumer electronic device to pass through the first window or opening.

6. A personal care device as claimed in claim 1, wherein the receiving member is configured such that the consumer electronic device is received and retained in or on the personal care device so that an imaging plane of the imaging unit of the consumer electronic device is perpendicular or substantially perpendicular to a plane of the first window or opening.

7. A personal care device as claimed in claim 1, wherein the receiving member comprises a recess provided in the housing and configured and shaped to receive the consumer electronic device in an at least partially submerged position in the housing.

8. A personal care device as claimed in claim 7, wherein the recess is shaped to enable consumer electronic devices having different sizes to be received and retained in the recess.

9. A personal care device as claimed in claim 7, wherein the personal care device further comprises a retaining mechanism configured to retain the consumer electronic device in the recess in a stationary position relative to the housing.

10. A personal care device as claimed in claim 9, wherein the retaining mechanism is configured to retain consumer electronic devices having different sizes in the recess.

11. A personal care device as claimed in claim 9, wherein the retaining mechanism comprises a cover plate that is configured to be placed over a part of the consumer electronic device when received in the recess to thereby retain the consumer electronic device in or on the personal care device.

12. A personal care device as claimed in claim 9, wherein the retaining mechanism comprises a plurality of cover plates, wherein each cover plate is configured to be placed over a part of a consumer electronic device having a respective size when received in the recess, wherein each cover plate is configured to retain the consumer electronic device having the respective size in or on the personal care device.

13. A personal care device as claimed in claim 1, wherein the personal care device is configured to perform the light-based hair removal or photo-epilation operation on a part of the body adjacent to the first window or opening.

14. A personal care device as claimed in claim 1, wherein the personal care device further comprises an aperture, and wherein the personal care device is configured to perform the light-based hair removal or photo-epilation operation on a part of the body adjacent to the aperture.

* * * * *